United States Patent [19]
Bien et al.

[11] Patent Number: 5,485,276
[45] Date of Patent: Jan. 16, 1996

[54] MULTI-PASS OPTICAL CELL SPECIES CONCENTRATION MEASUREMENT SYSTEM

[75] Inventors: Fritz Bien, Concord; Michael Gersh, Bedford; Neil Goldstein, Belmont; Jamine Lee, Burlington, all of Mass.

[73] Assignee: Spectral Sciences Inc., Burlington, Mass.

[21] Appl. No.: 310,666

[22] Filed: Sep. 22, 1994

[51] Int. Cl.⁶ .......................... G01N 21/31; G01N 21/59
[52] U.S. Cl. .......................... 356/437; 250/576; 356/440
[58] Field of Search ................... 356/436, 437, 356/440; 250/576

[56] References Cited

U.S. PATENT DOCUMENTS

| | | | |
|---|---|---|---|
| 3,524,066 | 8/1970 | Blakkan | 250/576 |
| 3,860,818 | 1/1975 | Stalder et al. | 356/437 X |
| 4,205,550 | 6/1980 | Swanson | 356/438 X |
| 4,549,080 | 10/1985 | Baskins et al. | 250/343 |
| 4,560,873 | 12/1985 | McGowan et al. | 356/339 |
| 4,736,360 | 4/1988 | McMahon . | |
| 4,884,891 | 12/1989 | Borsboom | 356/446 |
| 5,049,742 | 9/1991 | Hosonuma et al. | 356/70 X |
| 5,173,749 | 12/1992 | Tell et al. | 356/437 |
| 5,241,367 | 8/1993 | Grob et al. | 356/435 |
| 5,263,198 | 11/1994 | Fournier | 356/437 X |

FOREIGN PATENT DOCUMENTS

| | | | |
|---|---|---|---|
| 60-140141 | 7/1985 | Japan | 356/437 |
| 63-263447 | 10/1988 | Japan | 356/437 |
| 340946 | 6/1972 | U.S.S.R. | 356/436 |

OTHER PUBLICATIONS

Goldstein et al; Applied Optics, 20 Jun. 1992, vol. 31 #18 pp. 3409–3415.
Carlisle et al; Optics Letters; vol. 14 #23 sec I, 1989, pp. 1308—1308.
Goldstein et al "Multipoint Fiberoptic Humidity Monitor," Drying Tech. 9(4) 1991, pp. 833, 838–835.

*Primary Examiner*—Vincent P. McGraw
*Attorney, Agent, or Firm*—Iandiorio & Teska

[57] ABSTRACT

A multi-pass optical cell for measuring the concentration of one or more species in a fluid to be monitored includes a sample region; a source of collimated radiation; a detector device for sensing the intensity of the radiation; at least two reflective surfaces for reflecting in a first direction in the sample region a number of times the radiation from the source and delivering it to the detector device.

17 Claims, 4 Drawing Sheets

MULTI-PASS OPTICAL CELL SPECIES CONCENTRATION MEASUREMENT SYSTEM

FIELD OF INVENTION

This invention relates to a multi-pass optical cell system for measuring the concentration of one or more species in a fluid being monitored, and to such a system which is portable.

BACKGROUND OF INVENTION

The detection of concentrations of oxygen, carbon monoxide, carbon dioxide or other constituents or contaminants in ambient air has become ever more important in the pursuit of clean, healthy air. It is particularly difficult to obtain accurate readings in environments where the concentrations of different species are rapidly changing. Diode lasers have been used to measure atmospheric species. In diode laser systems a laser beam is directed through a sample volume or cell containing a gas or gasses each of which absorb laser energy at specified wavelengths. The type of gas in the cell can be determined by noting the wavelength of the energy absorbed or by supplying the cell with a known wavelength which corresponds to the absorption wavelength of a particular gaseous species of interest. The concentration of the gas can be computed from the pressure, the temperature, and the amount of absorption, which may be accomplished by comparing the amount of incident radiation to the amount of transmitted radiation: the greater the absorption, the greater the species concentration. To achieve the absorption in these systems a long optical path is typically required, which is generally accomplished by providing a cell or sample volume with a substantial height using multiple passes of light. In order to draw the atmospheric species into the cell, typically a pump is used. The pump is bulky and requires a substantial amount of power. Therefore these systems are not suitable for applications which require low profile and portable devices. More importantly, the pump causes a large pressure drop when activated. This pressure drop causes the density of the atmospheric species introduced to the cell to change, thereby resulting in an altered sample different than the ambient conditions being monitored. Accordingly, inaccurate readings of species concentration in ambient air are obtained. In addition, the pump, which is interconnected with the sample volume by a port that is usually smaller than the cross-sectional area of the sample volume, causes turbulence and recirculation of gases in the cell or sample volume which also affects the species concentration of the sample and the accuracy of species concentration measurement of the ambient air. Moreover, the height of the cell can limit the response time, which can deleteriously affect accuracy when dealing with changing ambient conditions. The pumping time to replace the gas in such a sample volume is typically long, taking several seconds to refresh the gas sample.

SUMMARY OF INVENTION

It is therefore an object of this invention to provide an improved optical cell system for measuring the concentration of one or more species in a fluid to be monitored.

It is a further object of this invention to provide such an improved optical cell system which provides long path absorption by utilizing a diode laser in a multi-pass arrangement to measure species concentration in the fluid.

It is a further object of this invention to provide such a multi-pass optical cell system with low power consumption.

It is a further object of this invention to provide such a multi-pass optical cell system which provides a relatively fast measurement response time.

It is a further object of this invention to provide such a multi-pass optical cell system which has a sampling region with a large fluid throughput and a relatively short height.

It is a further object of this invention to provide such a multi-pass optical cell system which draws fluid into a sampling region with very small pressure drop.

It is a further object of this invention to provide such a multi-pass optical cell system which draws fluid into a sample region without turbulence or deleteriously affecting the concentration of the sample.

It is a further object of this invention to provide such a multi-pass optical cell system which provides accurate species concentration measurement at inlet or ambient conditions.

It is a further object of this invention to provide such a multi-pass optical cell system which is easily sealed for calibration.

This invention results from the realization that a truly effective multi-pass optical cell system for accurately measuring the concentration of one or more species in a fluid being monitored may be accomplished by providing a sample region, a source of collimated radiation, a detector device and at least two reflective surfaces for reflecting in a first direction in the sample region a number of times the radiation from the source and delivering it to the detector device.

This invention features a multi-pass optical cell for measuring the concentration of one or more species in a fluid to be monitored. The cell includes a sample region, a source of collimated radiation, and a detector device for sensing the intensity of the radiation. There are at least two reflective surfaces for reflecting in a first direction in the sample region a number of times the radiation from the source and delivering it to the detector device.

In a preferred embodiment there may also be a fluid propellant device for moving the fluid to be monitored through the sample region in a second direction transverse to the first direction. The fluid propelling device may include a port for interconnecting with the sample region and the port may be approximately the same or greater in area than the sample region. The height of the sample region may be no greater than its diameter and the height may be substantially equal to the height of the collimated radiation reflected in the sample region. The source of collimated radiation may have a wavelength equal to the absorption wavelength of the species being monitored. The source of collimated radiation may be a laser diode. The detector may be a photodetector and the reflective surfaces may be plane mirrors. The fluid propellant device may be a fan. There may further be included means, responsive to the detector device, for measuring the concentration of the species being monitored.

This invention also features a multi-pass optical cell for measuring the concentration of one or more species in a fluid to be monitored. The cell includes a sample region, a source of collimated radiation, and a detector device for sensing the intensity of the radiation. There are at least two reflective surfaces for reflecting in a first direction in the sample region a number of times the radiation from a source and delivering it to the detector device and the sample region as a height which is no greater than its diameter.

In a preferred embodiment there may also be a fluid propellant device for moving the fluid to be monitored through the sample region in a second direction transverse to the first direction. The fluid propellant device may include a port for interconnecting with the sample region and the port may be approximately the same or greater in area than the sample region. The height of the sample region may be substantially equal to the height of the collimated radiation reflected in the sample region. The source of collimated radiation may have a wavelength equal to the absorption wavelength of the species being monitored. The source of collimated radiation may be a laser diode. The detector may be a photodetector and the reflective surfaces may be plane mirrors. The fluid propellant device may be a fan. There may further be included means, responsive to the detector device, for measuring the concentration of the species being monitored.

This invention further features a multi-pass optical cell system for measuring the concentration of one or more species in a fluid to be monitored. The system includes a sample region and a source of collimated radiation. There is also included a detector device for sensing the intensity of the radiation and at least two reflective surfaces for reflecting in a first direction in the sample region a number of times the radiation from the source and delivering it to the detector the device. There is also included a fluid propellant device for moving the fluid to be monitored through the sample region in a second direction transverse to the first direction. The fluid propellant device has a port for interconnecting with the sample region, the port being approximately the same or greater in area than the sample region.

In a preferred embodiment the height of the sample region may be no greater than its diameter and the height may be substantially equal to the height of the collimated radiation reflected in the sample region. The source of collimated radiation may have a wavelength equal to the absorption wavelength of the species being monitored. The source of collimated radiation may be a laser diode. The detector may be a photodetector and the reflective surfaces may be plane mirrors. The fluid propellant device may be a fan. There may further be included means, responsive to the detector device, for measuring the concentration of the species being monitored.

DISCLOSURE OF PREFERRED EMBODIMENT

Other objects, features and advantages will occur to those skilled in the art from the following description of a preferred embodiment and the accompanying drawings, in which.

Figure 1:
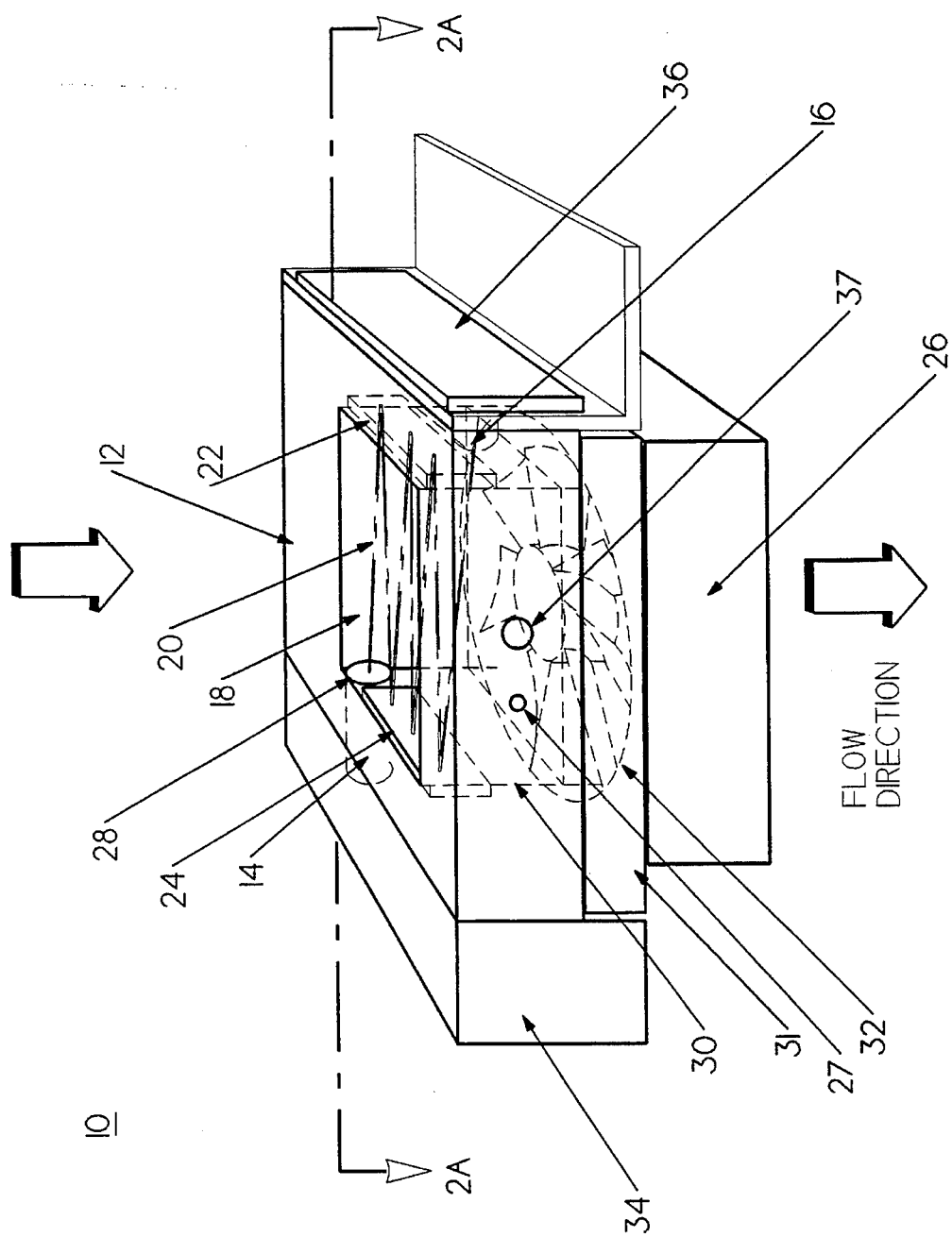
FIG. 1 is a three-dimensional perspective view of a multi-pass optical cell measuring system according to this invention.

The present invention uniquely achieves a long optical path for emitted radiation from a collimated light source by reflecting the radiation in the sample region a number of times between two reflective surfaces before delivering it to a detector and by introducing the fluid to be monitored to the sample region in a direction which is transverse to the direction of travel of the radiation. This provides the necessary long optical path while limiting the height of the sample region. As discussed above, prior art systems generally increase the height (and necessarily the volume) of the sample region to lengthen the optical path of the radiation. Minimizing the height of the sampling region has a number of advantageous results. First, since the height is minimized the overall size of the system can be reduced. Also, a less powerful fluid propellant device, such as a fan may be used to draw fluid into the sample region which causes little or no pressure drop when the fan is activated. Moreover, the port connecting the fan to the sample volume and the exit port of the sample volume are closely matched in size and are of large cross-sectional area, which also reduces the pressure drop and reduces turbulence in the sample volume caused by activation of the fluid propellant device. Reducing the pressure drop and turbulence within the sample volume as compared to prior art systems results in the introduction of a fluid sample into the sample volume which closely matches the ambient conditions under test. Accordingly, a more accurate species concentration measurement may be obtained. The fluid sample drawn into the sample volume with prior art high power pump systems undergoes a pressure change and is subjected to velocity gradients and turbulence. Thus, the density of the ambient sample changes as it enters the sample volume, turbulent recirculation mixes the new sample with previously sampled gases, and the concentration measurements of the species in the ambient air are deleteriously affected.

In addition, since the height of the sample region is minimized ambient air is quickly drawn through the sample region where species concentration measurements are taken. That is, there is a very short time lag between the time a sample of ambient air is located at the inlet to the sample region and the time it is located within the sample region and undergoing species concentration measurements. Accordingly, the system is very sensitive to changes in species concentrations in ambient air. This is critical to obtaining accurate measurements in environments where the concentrations of different species are rapidly changing.

Because the measurement system of the present invention is small in size and has low power requirements it is well suited for use as a portable unit. Moreover, the system may include a mechanism to maintain a wavelength "lock" on the absorption wavelength of species to be monitored, see U.S. Pat. No. 5,026,991 incorporated herein by reference in its entirety, so that the system may be inconspicuously located and activated for unattended measurement of the concentration of the species being monitored. The system may also be equipped with a mechanism to achieve the wavelength lock, thereby making the measurement system completely self sufficient after activation. Such a mechanism is described in a U.S. patent application by Lee et al. entitled "System And Method For Achieving Wavelength Lock", filed on even date herewith, which is incorporated herein by reference in its entirety.

There is shown in FIG. 1 a multi-pass optical cell species concentration measuring system 10 for measuring the concentration of one or more species in a fluid to be monitored, such as ambient air, which may contain for example oxygen, carbon monoxide, carbon dioxide or other constituents or contaminants. System 10 includes a multi-pass optical cell 12 which includes a collimated light source 14 which may be a laser diode such as a AlGaAs, InGaAsP, or any suitable laser, detector 16 which may be a photodetector, such as a germanium or silicon photodiode or any suitable detector, and sample region 18 through which a beam of radiation 20 propagates. The wavelength of the radiation is selected so that it matches the absorption wavelength of the species in the fluid being monitored. The radiation 20, after being emitted from light source 14, is reflected a number of times between plane mirrors 22 and 24 disposed on opposite sides of the sample region 18 until the radiation is received by detector 16.

In operation, fan 26 draws ambient air in through inlet port 28 of sample region 18 and it then passes the air through sample region 18 and out exit port 30 of sample region 18. The air then travels through apertured pass through plate 31 where it enters the inlet port 32 of fan 26. The air is eventually expelled through the fan outlet port (not shown). In applications where the system 10 is placed in a moving airstream produced by wind or vehicle motion, for example, the need for a fan is obviated. Light source electronics 34, such as those described in U.S. Pat. No. 5,026,991, control collimated light source 14 by operating the light source at the absorption wavelength of a particular species which is being monitored. As described above, the wavelength lock on the absorption wavelength of the species being monitored may be achieved and maintained after system activation so that it may operate unattended after initial activation. Detector 16 receives the light emitted from light source 14 and provides detector electronics 36 with an electrical signal proportional to the intensity of the radiation received by detector 16. Temperature and pressure probes 27 and 37, respectively, are mounted in sample region 18 to monitor the thermodynamic properties of the sampled gases and provide detector electronics 36 with signals indicative of these properties. By determining the change in intensity of the radiation transmitted by light source 14 and received by detector 16, caused by gases with certain measured thermodynamic properties, detector electronics 36 can determine the concentration of the particular absorption species being monitored. The species concentrations for discrete times are then stored and may be subsequently retrieved.

The entire system 10 is relatively small in size because of the low height requirements of sampling region 18 described below, (e.g., 5 cm in length, 5 cm in width, and 0.5 cm in height). Moreover, since a fan is utilized to draw in ambient air, the system has low power requirements and may be operated for extended periods of time on battery power. Thus, the system is compact, light and portable.

Figure 2C:
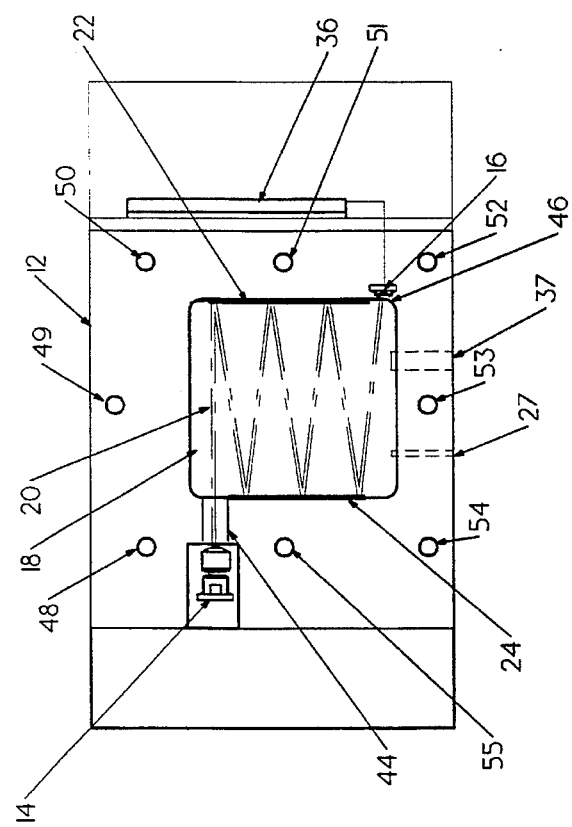
FIG. 2C is a top plan view of the system of FIG. 1.
Figure 2A:
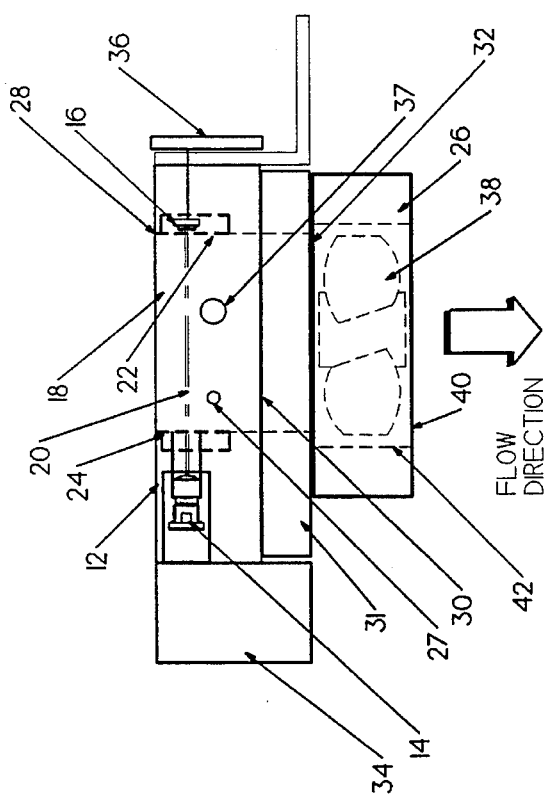
FIG. 2A is a cross-sectional view of the multi-pass optical cell measuring system taken along lines 2A—2A of FIG. 1.
Figure 2B:
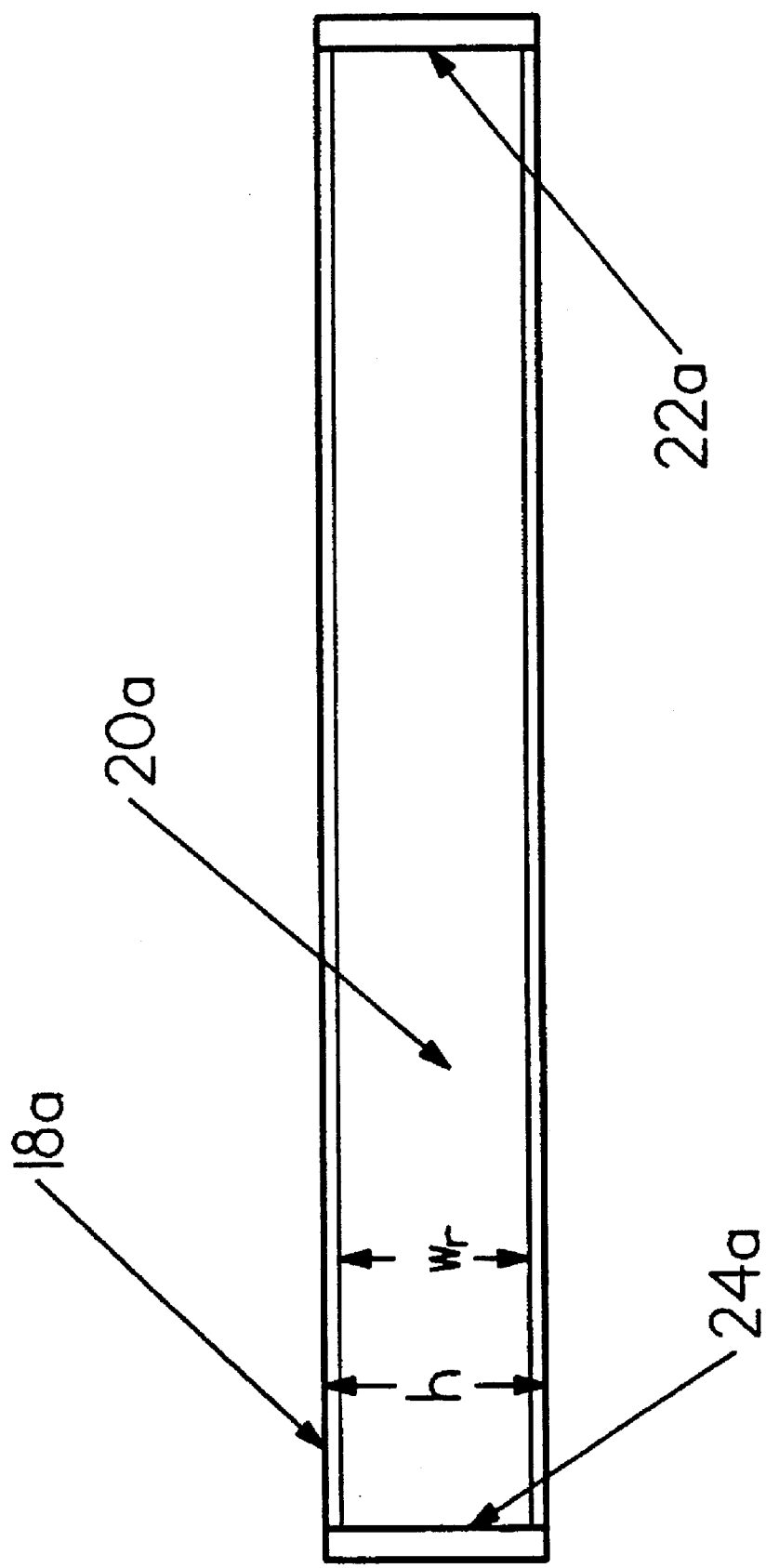
FIG. 2B is an enlarged cross-sectional view of the sample region of the multi-pass optical cell measuring system of FIG. 2A.

FIG. 2A depicts a cross-sectional view of species concentration monitoring system 10 of FIG. 1 taken along lines 2A—2A. In this view the propeller 38 (shown in phantom) in propeller cavity 40 of fan 26 is shown. The outer wall 42 of propeller cavity 40 terminates at inlet port 32. Inlet port 32 is configured to have approximately the same or greater diameter (area) as exit port 30 of sample region 18. The sample region 18 is defined by a relatively short height h. The height h is at a maximum equal to the diameter D of sample volume 18 and the inlet port 32 has the same or a greater diameter (area) as exit port 30 to allow a low power consumption fan to be used as opposed to a high power consumption pump. A fan draws, e.g., tenths of a watt of power, as opposed to a pump drawing, e.g., hundreds of watts of power. Moreover, the short height h allows for rapid passage through the sample region of the ambient air being monitored. The fan size coupled with the short height h of region 18 allow for a clean intake and air flow through sample region 18 of the ambient air with little or no turbulence or boundary layer buildup and little pressure drop. Because there is little or no turbulence or pressure drop a very accurate sample (one which closely approximates the ambient air) is introduced into sample region 18. Since the sample introduced to region 18 closely approximates the ambient air conditions, very accurate measurements of species concentration may be made. Moreover, since the height h is so short the fluid or ambient air introduced into sample region 18 is quickly passed through sample region 18 by fan 26 (at e.g. 10 meters per second). This allows for very fast measurement response of ambient air thus providing real time species concentration measurement. The height h of sample region 18 may be reduced to increase the measurement response to changes in species concentration in ambient air making the measurement system more sensitive to rapid concentration changes over time. It also increases the accuracy of species concentration measurement as the sample introduced into the sample region 18 more closely approximates the true ambient conditions. For optimum response time, the height h of sample region 18a, FIG. 2B, may be made as short as the width $w_1$ of radiation beam 20a. The width of the radiation beam may be equal to the diameter of beam 20a or it may be slightly wider if the radiation reflected between mirrors 22a and 24a does not remain in the same plane.

FIG. 2C is a top plan view of the measurement system of FIG. 1. In this figure the path of radiation beam 20 is clearly shown. The path begins where the radiation is generated at light source 14 and enters sample region 18 through entrance aperture 44 and is reflected back and forth between mirrors 22 and 24 until it exits sample region 18 through exit aperture 46 and is received by detector 16. The path between entrance aperture 44 and exit aperture 46 in sample region 18 may vary; however, the radiation beam 20 must propagate in a first direction from entrance aperture 44 to exit aperture 46, transverse to the fluid flow direction, which in this case is into the page.

There are also shown holes 48–55 for receiving screws 72 to affix a calibration cover (shown in FIG. 3A) which is utilized during the calibration procedure. There are a like number of holes (not shown) threaded to capture screws from holes 48–55 in the blanking plate 64 (also shown in FIG. 3A) on the opposite surface of optical cell 12 to close off the sample volume to the ambient air.

Figure 3B:
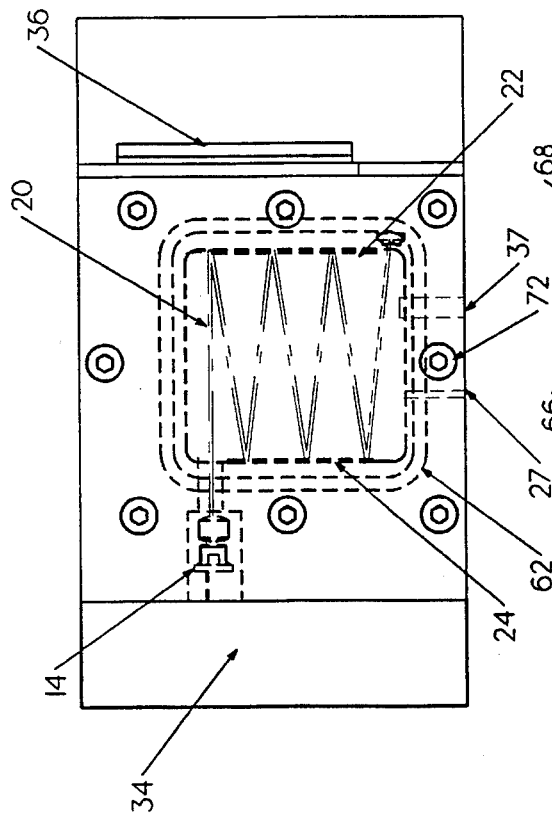
FIG. 3B is a top plan view of the optical cell measuring system of FIG. 1 similar to the view of FIG. 2C with "O"-rings installed about the inlet and exit ports of the sample volume during calibration.
Figure 3A:
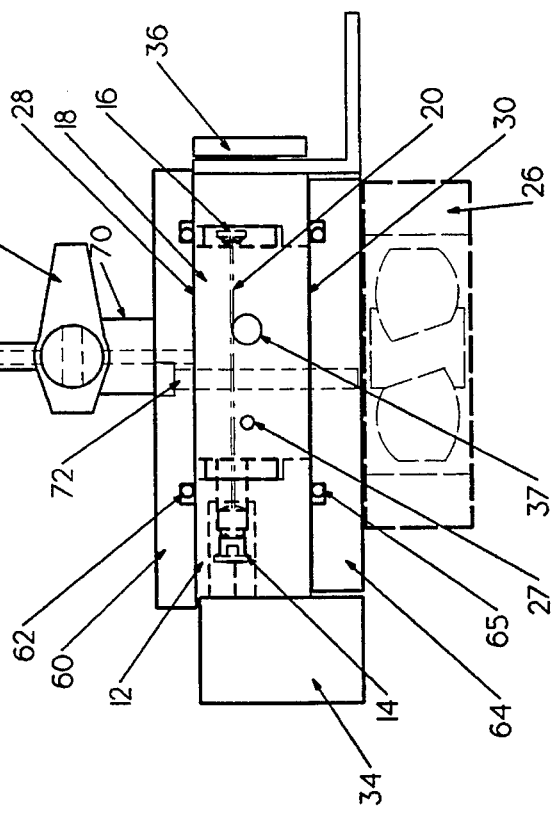
FIG. 3A is the same cross-sectional view as depicted in FIG. 2A with a calibration cover and blanking plate in place for performing system calibration.

During the calibration procedure calibration cover 60, FIG. 3A, which covers inlet port 28 and blanking plate 64 which covers exit port 30 of sample region 18 are installed. Also, "O"-rings 62 and 65 are installed about inlet port 28 and outlet port 30 of sample region 18 to seal sample volume 18 during calibration. During calibration of a particular species, e.g., oxygen, carbon monoxide or carbon dioxide, the cell is first evacuated. A sample containing a known concentration of the species is introduced into sample volume 18 by means of tubing 66, 70 and sealed by valve 68. Temperature and pressure probes 27 and 37 inserted into the sample region measure the thermodynamic properties of the sample and provide the measurements to detector electronics 36.

The radiation beam 20 is introduced to sample region 18 with a known intensity and propagated through sample region 18 where a portion of its intensity is lost or absorbed by the known species concentration in sample region 18. Detector 16 then receives the attenuated radiation beam and supplies detector electronics 36 with an electrical signal proportional to the beam's optical intensity. From this reduction in intensity due to the absorption by the species at the species absorption wavelength for the known concentration of species, and from a measurement of the sample temperature and pressure, the measurement system may be properly calibrated as is known. The system may be calibrated for a number of different species with different absorption wavelengths as is also known.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A multi-pass optical cell system for measuring the concentration of one or more species in a fluid to be monitored, comprising:
   a sample region;
   a source of collimated radiation;
   a detector device for sensing the intensity of said radiation;
   at least two reflective surfaces for reflecting in a first direction in said sample region a number of times the radiation from said source and delivering it to said detector device; and
   a fluid propellant device for moving the fluid to be monitored through said sample region in a second direction traverse to said first direction;
   said fluid propellant device having a port for interconnecting with said sample region, said port being approximately the same or greater in area than said sample region.

2. The multi-pass optical cell system of claim 1 in which the height of said sample region is no greater than its diameter.

3. The multi-pass optical cell system of claim 1 in which the height of said sample region is substantially equal to the width of said collimated radiation reflected in said sample region.

4. The multi-pass optical cell system of claim 1 in which said source of collimated radiation has a wavelength equal to the absorption wavelength of the species being monitored.

5. The multi-pass optical cell system of claim 1 in which said source of collimated radiation is a laser diode.

6. The multi-pass optical cell system of claim 1 in which said detector is a photodetector.

7. The multi-pass optical cell system of claim 1 in which said at least two reflective surfaces are plane mirrors.

8. The multi-pass optical cell system of claim 1 in which said fluid propellant device is a fan.

9. The multi-pass optical cell system of claim 1 further including means, responsive to said detector device, for measuring the concentration of the species being monitored.

10. A multi-pass optical cell system for measuring the concentration of one or more species in a fluid to be monitored, comprising:
    a sample region;
    said sample region having a height which is no greater than its diameter;
    a source of collimated radiation;
    a detector device for sensing the intensity of said radiation;
    at least two reflective surfaces for reflecting in a first direction in said sample region a number of times the radiation from said source and delivering it to said detector device; and
    a fluid propellant device for moving the fluid to be monitored through said sample region in a second direction transverse to said first direction;
    said fluid propellant device having a port for interconnecting with said sample region, said port being approximately the same or greater in area than said sample region.

11. The multi-pass optical cell system of claim 10 in which the height of said sample region is substantially equal to the width of said collimated radiation reflected in said sample region.

12. The multi-pass optical cell system of claim 10 in which said source of collimated radiation is a wavelength equal to the absorption wavelength of the species being monitored.

13. The multi-pass optical cell system of claim 10 in which said source of collimated radiation is a laser diode.

14. A multi-pass optical cell system of claim 10 in which said detector is a photodetector.

15. The multi-pass optical cell system of claim 10 in which said at least two reflective surfaces are plane mirrors.

16. The multi-pass optical cell system of claim 10 in which said fluid propellant device is a fan.

17. The multi-pass optical cell system of claim 10 further including means, responsive to said detector device, for measuring the concentration of the species being monitored.

* * * * *